United States Patent
Bergamaschi

(10) Patent No.: US 11,931,044 B2
(45) Date of Patent: Mar. 19, 2024

(54) PERCUTANEOUS DEVICE FOR CLOSING BLOOD VESSELS

(71) Applicant: VCD MEDICAL S.R.L., Brescia (IT)

(72) Inventor: Gastone Bergamaschi, Verona (IT)

(73) Assignee: VCD MEDICAL S.R.L., Brescia (IT)

( * ) Notice: Subject to any disclaimer, the term of this patent is extended or adjusted under 35 U.S.C. 154(b) by 216 days.

(21) Appl. No.: 17/551,834

(22) Filed: Dec. 15, 2021

(65) Prior Publication Data
US 2023/0181193 A1 Jun. 15, 2023

(51) Int. Cl.
*A61B 17/128* (2006.01)
*A61B 17/00* (2006.01)
*A61B 17/122* (2006.01)

(52) U.S. Cl.
CPC ........ *A61B 17/1285* (2013.01); *A61B 17/122* (2013.01); *A61B 2017/00004* (2013.01)

(58) Field of Classification Search
CPC ........ A61B 17/122; A61B 2017/00584; A61B 2017/00606; A61B 2017/00615; A61B 2017/00637; A61B 2017/00641; A61B 2017/00668; A61B 2017/0419; A61B 17/0487; A61B 17/08; A61B 2017/081; A61B 17/083; A61B 17/1285; A61B 17/132; A61F 6/20; A61F 6/202; A61F 6/204; A61F 6/206; A61F 2002/047; A61F 2002/048; A61F 2/0004; A61F 2/0009; A61F 2/0013; A61F 2/0018; A61F 2/0022; A61F 2/0027; A61F 2/003
See application file for complete search history.

(56) References Cited

U.S. PATENT DOCUMENTS

| | | | | |
|---|---|---|---|---|
| 2006/0229623 A1* | 10/2006 | Bonutti | ............ | A61B 17/8863 606/74 |
| 2008/0033488 A1* | 2/2008 | Catanese, III | ..... | A61B 17/0487 606/232 |
| 2016/0120546 A1* | 5/2016 | Roundy | ............ | A61B 17/1285 606/143 |
| 2019/0117211 A1 | 4/2019 | Catanese et al. | | |

FOREIGN PATENT DOCUMENTS

| | | |
|---|---|---|
| ES | 2709683 A1 | 4/2019 |
| WO | 2010/127083 A2 | 11/2010 |
| WO | 2014/102767 A2 | 7/2014 |

* cited by examiner

*Primary Examiner* — Shaun L David
*Assistant Examiner* — Rachael L Geiger
(74) *Attorney, Agent, or Firm* — ArentFox Schiff LLP; Michael Fainberg

(57) ABSTRACT

A percutaneous device for closing blood vessels has a main body in which a distal clip and a proximal clip connected to each other by a tie rod are accommodated, an abutment element, and a handle for maneuvering the distal and proximal clips, the abutment element and the tie rod. The distal clip has a proximal housing, and the proximal clip has a distal housing and a proximal housing. The tie rod is positioned inside the housings when the distal and proximal clips are inserted inside the main body, so as to not interfere with correct sliding thereof.

8 Claims, 16 Drawing Sheets

PERCUTANEOUS DEVICE FOR CLOSING BLOOD VESSELS

FIELD OF THE INVENTION

The present invention relates to a device for interrupting the function of superficial venous collectors, using percutaneous access and ultrasonic guidance.

BACKGROUND OF THE INVENTION

Surgical treatment for superficial venous insufficiency of the lower limbs has undergone dramatic development in recent decades. A widespread need for less invasive surgery has been demonstrated, and technological evolution has rendered the most traumatic procedures, such as the Linton operation, obsolete, while standard procedures, such as saphenous vein stripping, have scaled back in favor of low-invasive procedures, such as ablation of superficial venous collectors by thermal techniques (laser, radiofrequency) or non-thermal techniques (sclerosis foam, mechanochemical ablation, and cyanoacrylate glues), not to mention surgical strategies such as endoscopic subfascial ligation of perforating veins or saphenous reflux segmentation.

Some of the aforementioned known techniques are intended for well-defined niche pathologies, whereas others are, in the absence of a clear hierarchy, valid alternative therapies in terms of efficacy, reduction of complications, long-term results and costs.

It is nevertheless noted that "surgical" techniques are linked to invasiveness and a significant risk of complications, while endoluminal ablative techniques entail a share of long-term failures (recanalizations) and involve a likelihood, albeit very small, of serious complications. With regard to ablative techniques, it is widely believed that the point of maximum criticality in the methodology may be found in the sapheno-femoral confluence, i.e. the short venous site which, in the event of over- or under-treatment, may place the patient at risk of thrombosis that extends to deep circulation or central embolism and at risk of more or less extensive recanalization of the vessel by blood reflux, with recurrence of the varicose syndrome.

In the field of treating superficial venous insufficiency of the lower limbs, there is therefore a strong need to carry out a procedure which is to all effects "surgical," such as interruption in order to ligate a venous collector, without exposing the patient to the invasiveness and the preventable complications involved therewith.

SUMMARY OF THE INVENTION

The object of the present invention is to provide a percutaneous device for interrupting the function of venous collectors that makes it possible to mechanically occlude a venous vessel by means of transcutaneous puncture access.

This object is achieved by a percutaneous device for interrupting the function of venous collectors as described and claimed herein.

The percutaneous device according to the present invention makes it possible to carry out operations to intercept and/or close blood vessels using percutaneous access in a simplified manner, which requires reduced manual ability which is not necessarily surgical. As a result, operating time and impact on patient acceptance (or compliance) are drastically reduced compared with "open" surgery techniques.

BRIEF DESCRIPTION OF THE FIGURES

Further advantages of a percutaneous device according to the present invention will become apparent from the following description, given by way of non-limiting example and in accordance with the accompanying figures, in which:

FIG. 16A shows puncturing the venous vessel;

FIG. 16B shows releasing the distal clip;

FIG. 16C shows pulling the distal clip against the vessel;

FIG. 16D shows releasing the proximal clip;

FIG. 16E shows pushing the proximal clip against the vessel;

FIG. 16F shows clamping the clips and closing the vessel;

Figure 1A:
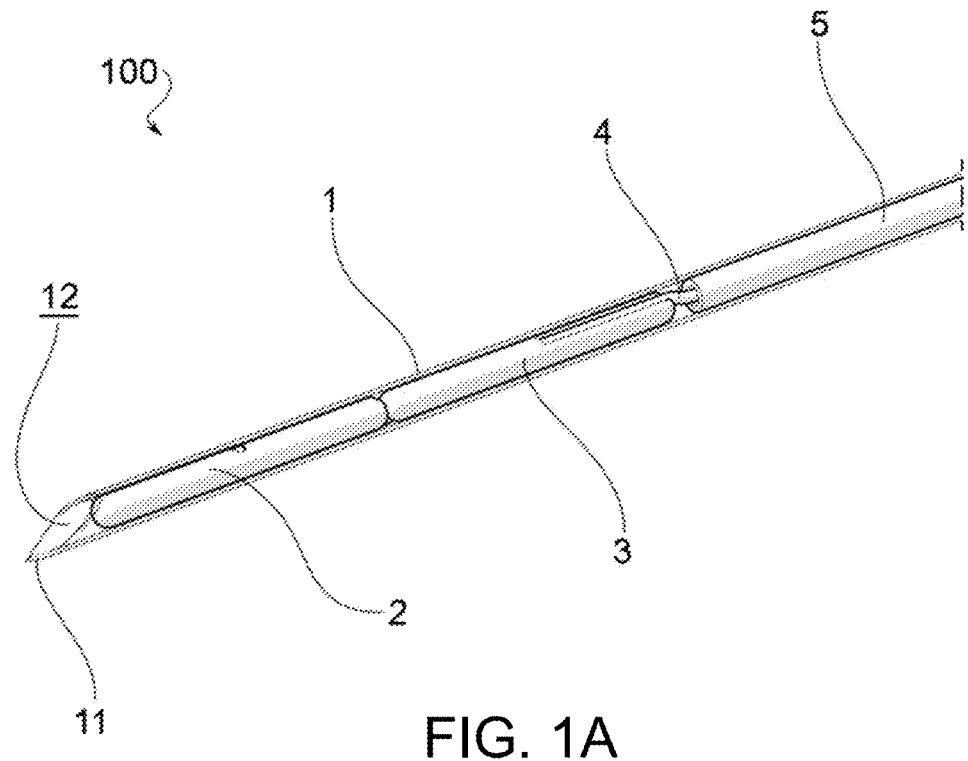
FIG. 1A shows a device according to the present invention in a configuration for percutaneous insertion.

In the figures, similar components are identified in different figures by the same reference sign.

DETAILED DESCRIPTION

Reference sign 100 represents a percutaneous device for interrupting the function of superficial venous collectors and closing a blood vessel, for example the saphenous vein.

The percutaneous device 100 comprises a main body 1 which extends along a longitudinal axis X and is internally hollow to house a pair of clamping clips 2, 3 and an abutment element 5 for the clips 2, 3.

The main body 1 is preferably a metal cannula which may be inserted percutaneously, and is provided with a distal tip 11. The distal tip 11 comprises a distal opening 12 from which the clips 2, 3 exit.

Figure 1B:
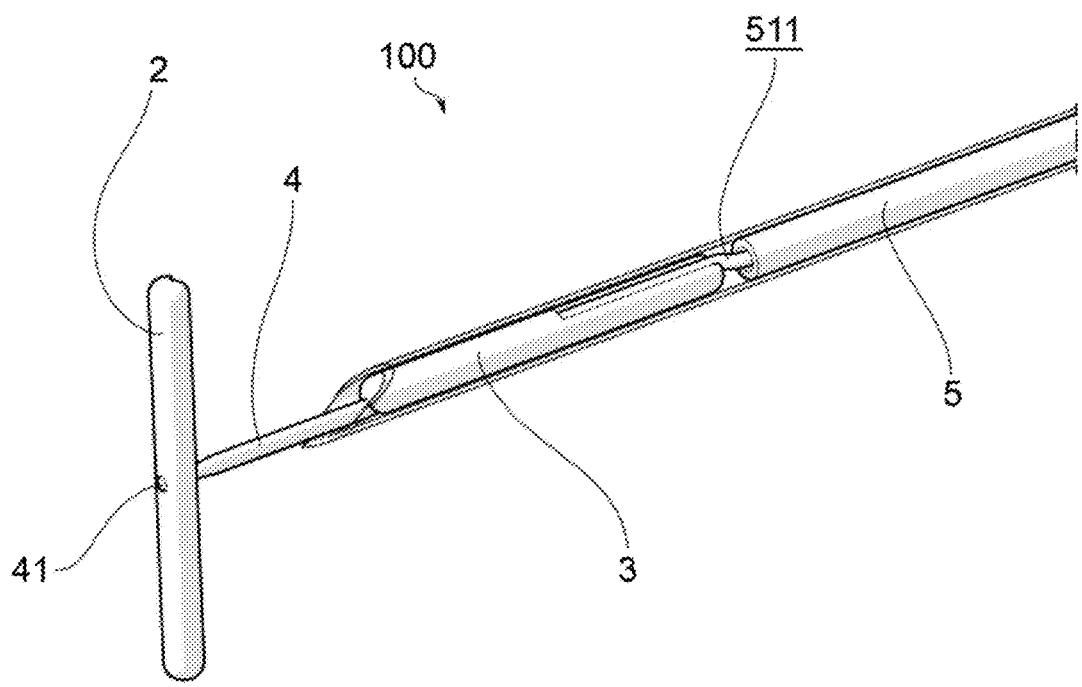
FIG. 1B shows a device according to the present invention in a configuration for release of the distal clip.
Figure 11A:
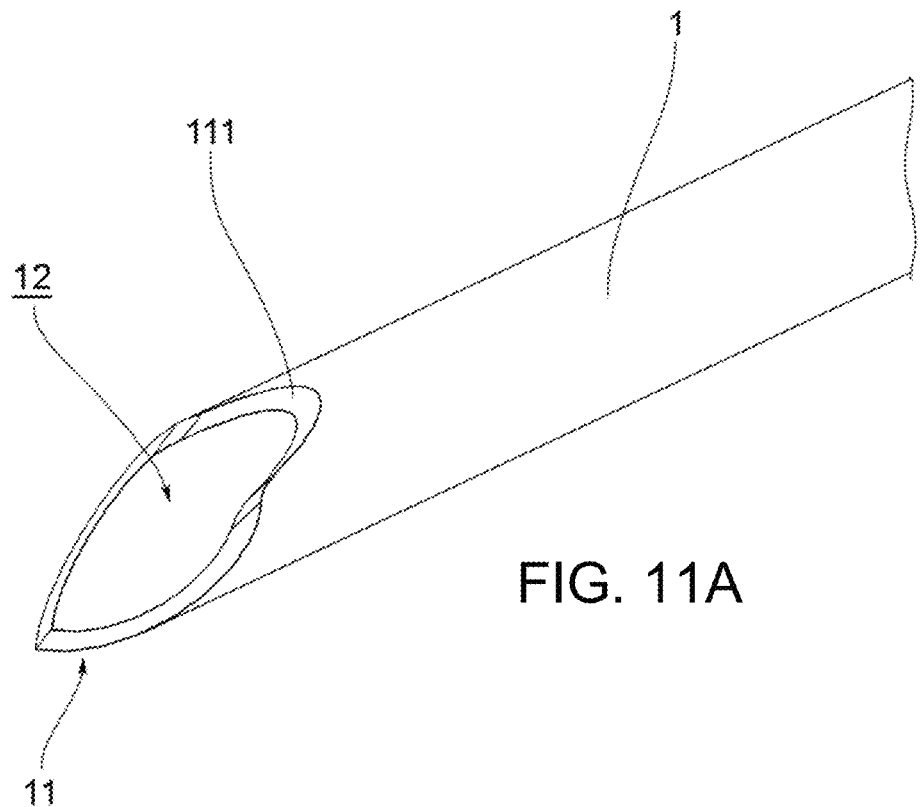
FIGS. 11A and 11B show the device according to the present invention wherein the main body has a distal perforation tip.
Figure 11B:
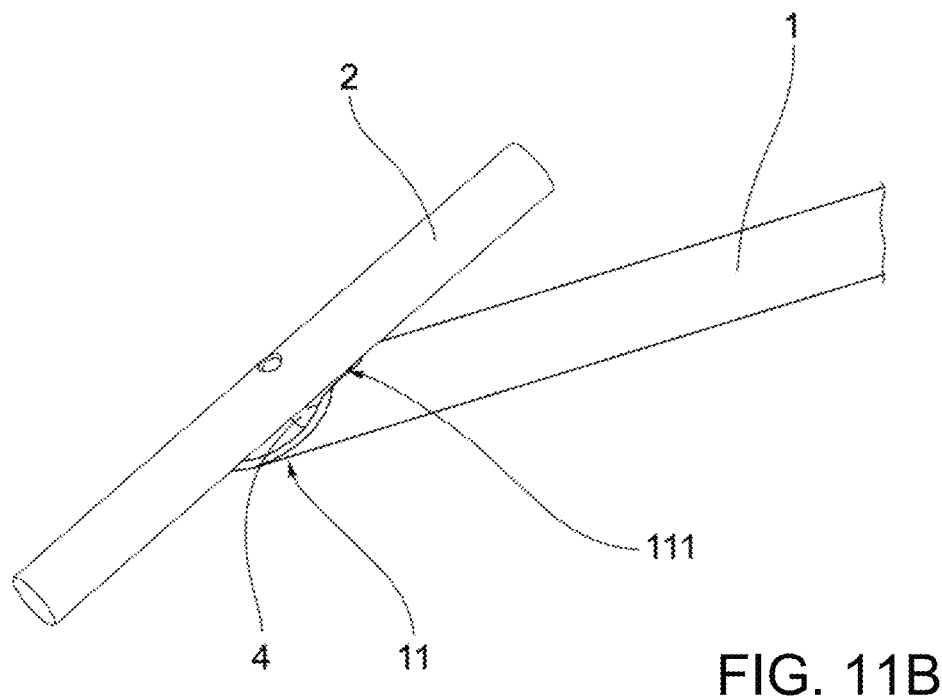

In one example, shown in FIGS. 1A and 11A, the distal tip 11 is a perforation tip, shaped as a needle to puncture the wall of a blood vessel V and to pass through the blood vessel from one side to the other. Preferably, the distal tip 11 of the main body 1 has a notch 111 that extends in the proximal direction. The notch 111 is sized to at least partially house the distal clip 2 in the releasing phase (FIG. 11B). The notch 111 is used as an abutment element to push the distal clip 2 towards the correct transverse position during the releasing phase (FIG. 1B).

Figure 10A:
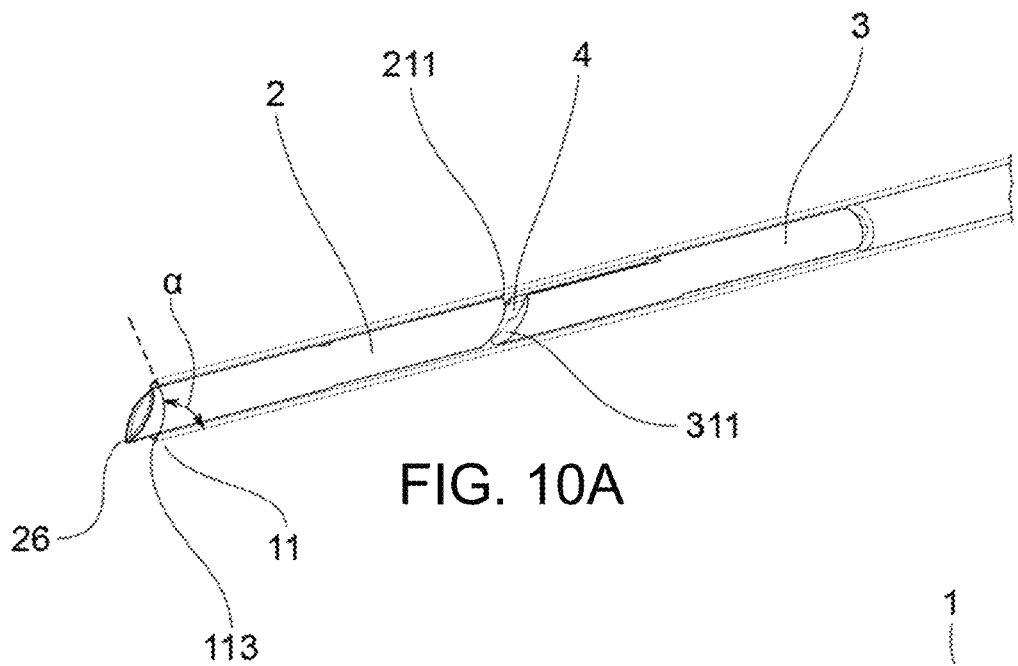
FIGS. 10A and 10B show the device according to the present invention having a further configuration of the clips.

In a different example, shown in FIG. 10A, the distal tip 11 is not a perforation tip. In said example, a perforation tip 112 is provided on the distal clip 2, as better explained hereinafter. When the distal tip 11 of the main body 1 is not a perforation tip, the distal tip 11 has a distal face 113 inclined of an angle α between 90° and 45° for a better pushing the distal clip 2 towards the correct transverse position. The distal tip 11 may have also a notch 111 to at least partially house the distal clip 2.

The abutment element 5 is preferably a rod which may be cylindrical, elliptical or semi-circular.

The abutment element 5 extends along the longitudinal axis X and is provided with a passageway for the tie rod 4. The passageway for the tie rod 4 is, for example, a hole 511 such that the tie rod 4 slides internally in the abutment element 5, or a lateral groove such that the tie rod 4 slides externally to the abutment element 5. The abutment element 5 is provided with a distal end 51 configured to push the proximal clip 3.

Figure 1C:
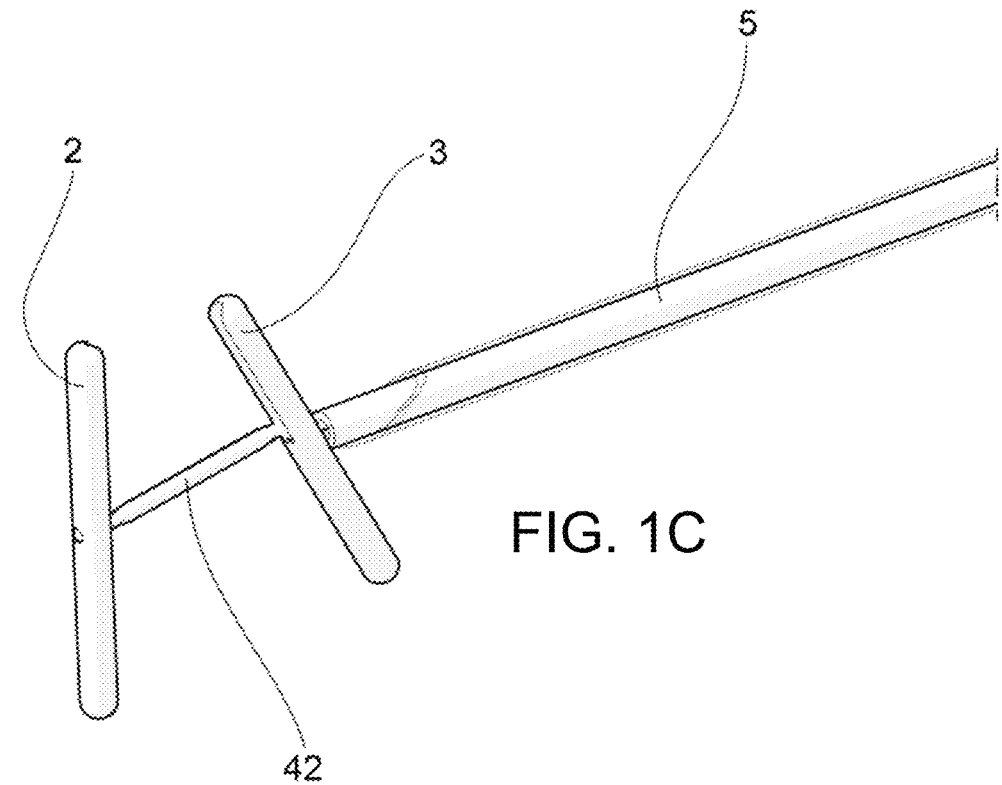
FIG. 1C shows a device according to the present invention in a configuration for release of the proximal clip.
Figure 1D:
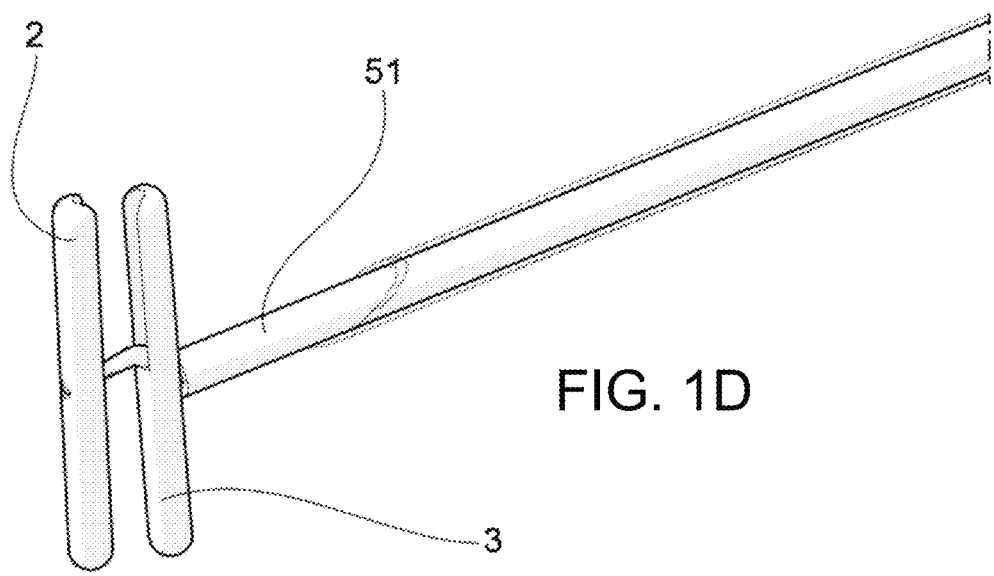
FIG. 1D shows a device according to the present invention in a configuration for closing a venous vessel.
Figure 12A:
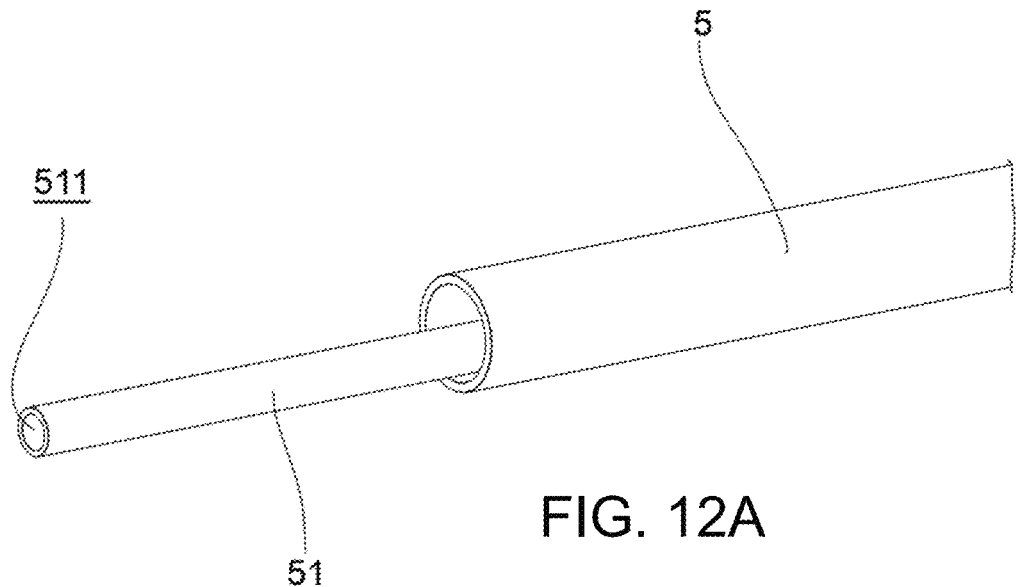
FIGS. 12A and 12B show the device according to the present invention having a further configuration of the abutment element.
Figure 12B:
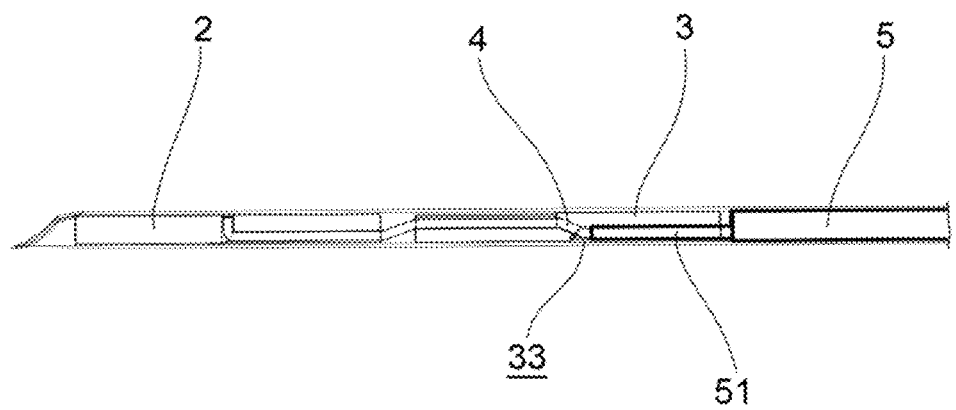

In the example of FIGS. 12A and 12B the distal end 51 of the abutment element 5 is sized to be housed in the proximal housing 33 of the proximal clip 3 (FIG. 12B). This solution allows positioning the distal end 51 of the abutment element 5 very close to the pivoting point of proximal clip 3 (that is the seat 31), improving pushing of the proximal clip 3 towards the correct transverse position during the releasing phase (FIG. 1C).

The percutaneous device 100 preferably comprises a handle 7 which is connected to the proximal portion of the main body 1 and is configured to maneuver the clips 2, 3 and the tie rod 4.

The overall configuration of the percutaneous device 100 is such that the pair of clamping clips 2, 3 and the abutment element 5 may be slidably inserted inside the main body 1, may exit from the distal opening 12, and may be maneuvered from the outside by means of the handle 7. It should be noted that the abutment element 5 is integral with the handle 7.

The pair of clips comprises a distal clip 2 for intercepting the vessel and a proximal clip 3 for clamping the vessel.

The clips 2, 3 are preferably substantially in the form of a bar or rod, i.e. they have a cylindrical and elongate shape.

Figure 10B:
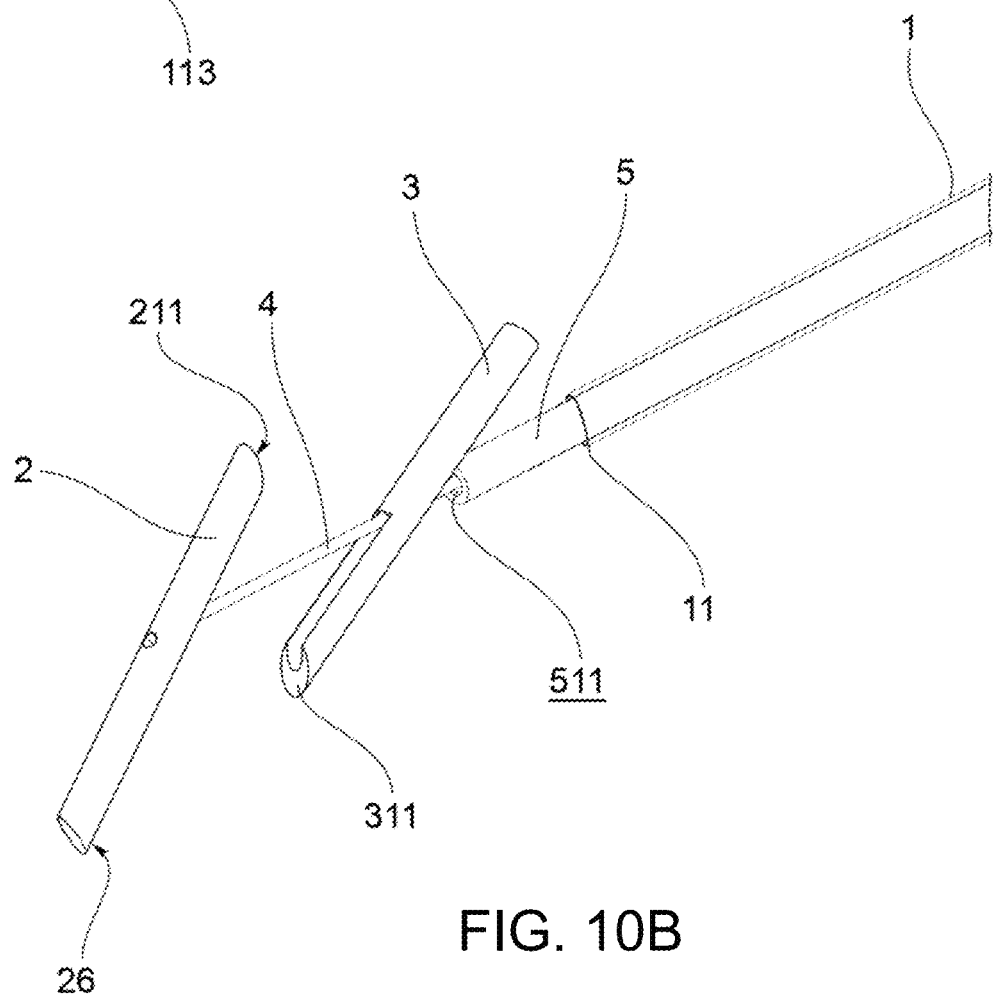

In the example of FIGS. 10A and 10B, the ends 211,311 faced one to each other of the clips 2,3 are shaped to allow a partial overlapping of the clips when inserted into the main body 1 (FIG. 10a). In this example, the clips 2, 3 have a solid and cylindrical body and the ends 211,311 have parallel inclined faces. This solution allows the clips 2, 3 to be correctly aligned with respect to the rotation plane, facilitating transverse positioning in the releasing phase.

When the distal tip 11 of the main body 1 is not a perforation tip, as in FIG. 10A, a perforation tip is provided on the distal clip 2. In this case, the distal clip 2 has a distal perforation end 26 shaped as a needle to puncture the wall of a blood vessel V and to pass through the vessel from one side to the other. In said example, at least the distal perforation end 26 of the distal clip 2 exits from the distal opening 12 of the main body 1, as shown in FIG. 10A.

Each clip 2, 3 preferably has a length determined by the specific surgical requirements and by the dimensions of the vessel to be treated, for example in a range of approximately 6-12 mm.

The clips 2, 3 may be the same length or may be different lengths.

The clips 2, 3 are preferably made of biocompatible metal material or of bioresorbable material.

The clips 2, 3 are connected to each other by a tie rod 4 or an equivalent means.

In one embodiment, shown in FIG. 1B, the tie rod 4 has a substantially circular or semi-circular cross section.

Figure 6A:
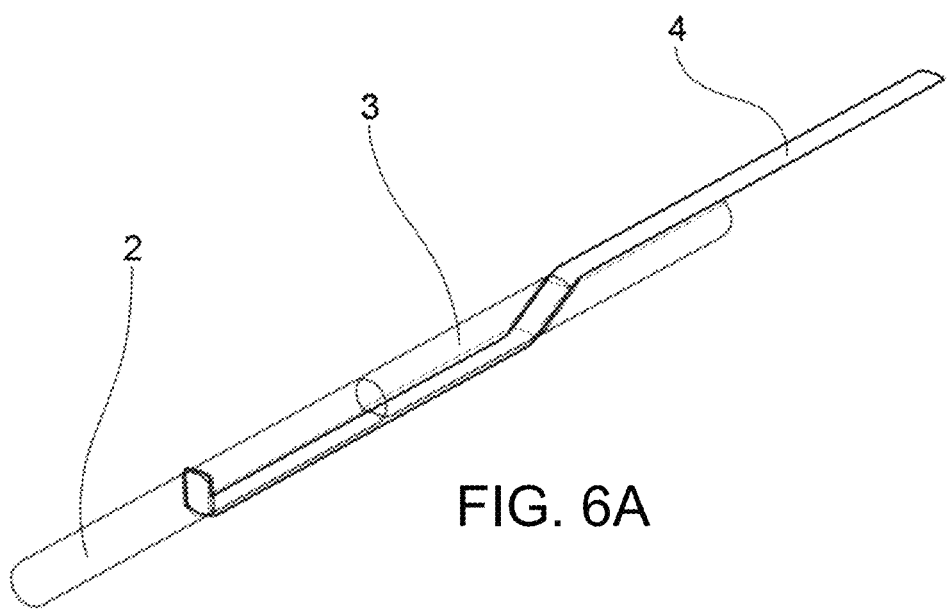
FIGS. 6A and 6B show a device according to the present invention in one embodiment comprising a flattened tie rod.

In a further embodiment, shown in FIG. 6A, the tie rod 4 has a flattened cross section or is substantially a tape.

In yet a further embodiment, the tie rod 4 has a flattened cross section distally, preferably between the two clips 2, 3, and then continues with a circular cross section proximally. In this embodiment, the tie rod 4 has a flattened cross section for a distal length between the length of half a clip and the length of two clips.

The tie rod 4 is preferably made of nylon or polyester or of resorbable material.

The clips 2, 3 are provided with a seat 21, 31 into which the tie rod 4 is inserted.

The distal clip 2 is provided with a distal seat 21 into which the tie rod 4 is fastened.

The distal seat 21 is preferably a through hole which has a circular (FIGS. 2 and 4) or rectangular cross section.

The distal seat 21 preferably transversely crosses the distal clip 2 perpendicularly. This solution makes it possible to correctly orient and turn over the distal clip 2 once it has been released.

The proximal clip 3 is provided with a proximal seat 31 into which the tie rod 4 is slidably inserted.

The proximal seat 31 is preferably a through hole which has a circular (FIG. 5A), oval (FIG. 5B) or rectangular (FIG. 8A) cross section.

The proximal seat 31 preferably transversely crosses the proximal clip 3 obliquely. This solution makes it possible both to correctly orient the proximal clip 3 once it has been released and to correctly slide the tie rod 4.

In particular, a distal end 41 of the tie rod 4 is fastened in the seat 21 of the distal clip 2, the tie rod 4 is also slidably inserted in the seat 31 of the proximal clip 3 such that an intermediate portion 42 of the tie rod 4 is arranged between the clips 2, 3, and a proximal end 43 of the tie rod 4 may be maneuvered by the surgeon, either directly or by the handle 7.

Depending on the specific application, the tie rod 4 and the clips 2, 3 may be to made of non-resorbable or resorbable material.

The clips 2, 3 preferably have transverse dimensions (i.e. a diameter) so as to be able to slide freely, possibly with minimal friction to prevent slipping, inside the main body 1.

When the clips 2, 3 are inserted inside the main body 1, the longitudinal axis of the clips 2, 3 is in line with the longitudinal axis of the main body 1.

One essential aspect for the correct functioning of the percutaneous device 100 is the positioning of the tie rod 4 inside the main body 1. The tie rod must not interfere with the correct sliding of the clips 2, 3.

The clips 2, 3 are therefore provided with at least one housing 22, 32, 33 in which the tie rod 4 is positioned when the clips 2, 3 are inside the main body 1.

The housing 22, 32, 33 is a longitudinal groove formed on the outer surface of the clip 2, 3 such that the tie rod 4 is inserted into the groove and therefore fits inside the volume of space occupied by the clip 2, 3, as shown in FIGS. 1A and 6A.

The distal clip 2 is provided with a proximal housing 22, and optionally also a distal housing for fastening the tie rod.

The proximal clip 3 is provided with both a distal housing 32 and a proximal housing 33.

Preferably, the housings are longitudinal grooves on the outer surface of the clips 2, 3 and the proximal housing 22 of the distal clip 2 occupies at least a proximal portion of the distal clip 2, the distal housing 32 of the proximal clip 3 occupies at least a distal portion of the proximal clip 3 and the proximal housing 33 of the proximal clip 3 occupies at least a proximal portion of the proximal clip 3.

The distal housing and the proximal housing are arranged on opposite sides of the clip.

Figure 2:
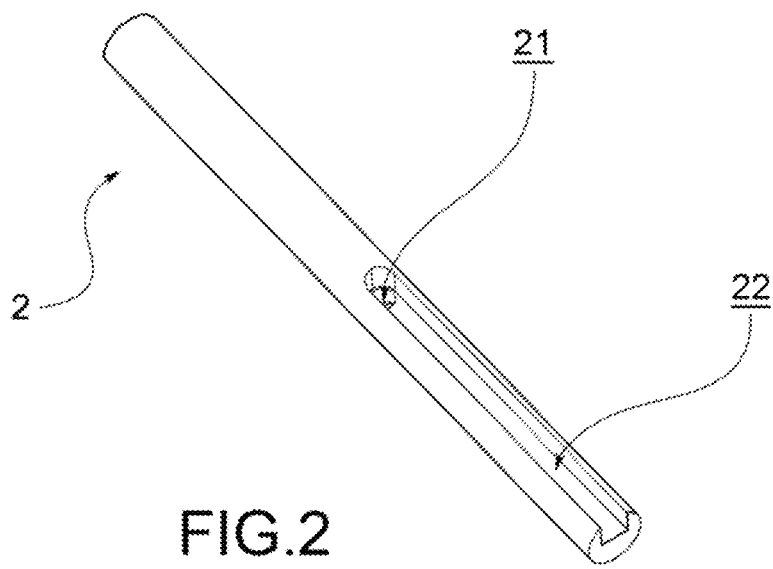
FIG. 2 is an axonometric view of the distal clip in one embodiment comprising a slot which is adapted to receive the tie rod element and has a U-shaped cross section.
Figure 3A:
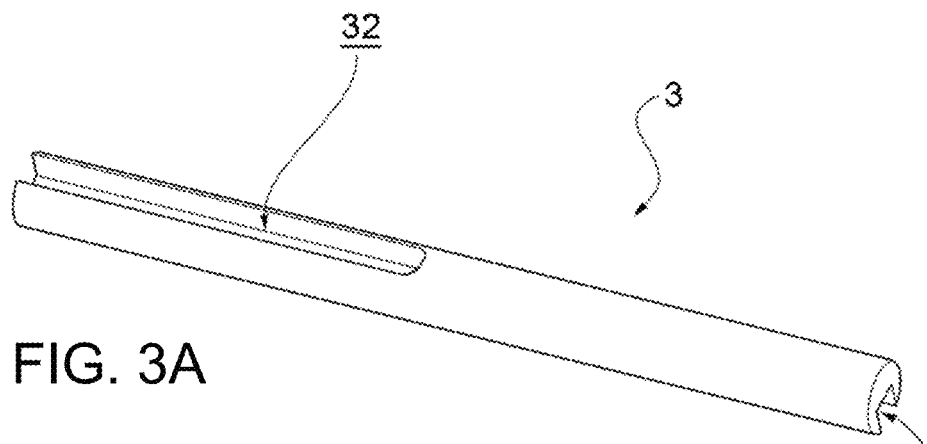
FIGS. 3A and 3B are an axonometric view and a cross-sectional view, respectively, of the proximal clip in one embodiment.
Figure 3B:
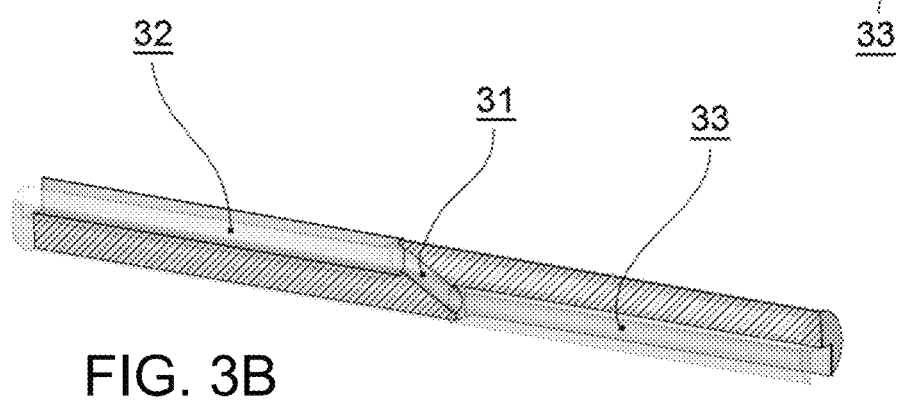
Figure 9A:
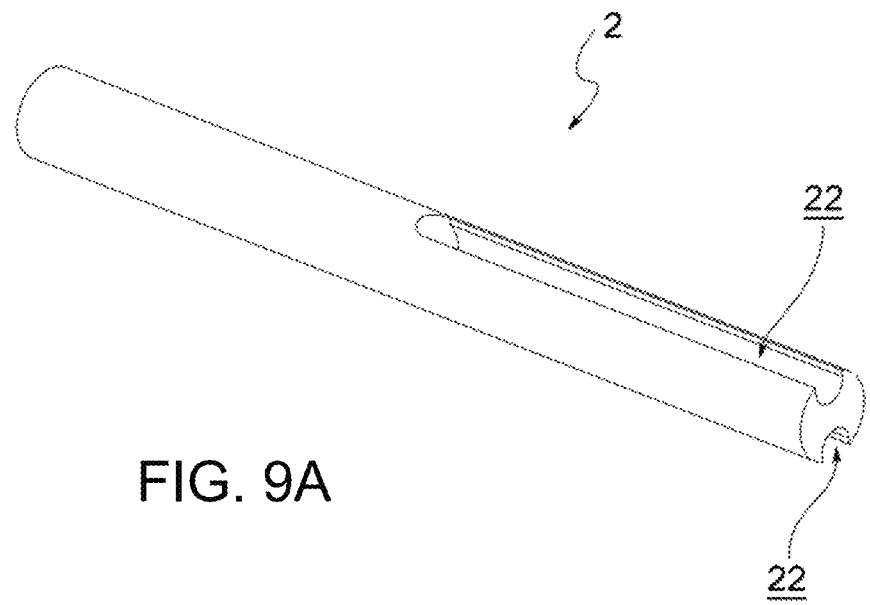
FIGS. 9A and 9B show the distal clip in one embodiment comprising two slots adapted to receive the tie rod element.

In one embodiment, shown in FIGS. 2, 3A and 9A, the housing 22, 32, 33 has a rectangular or square or U-shaped or semicircle cross section.

Figure 4:
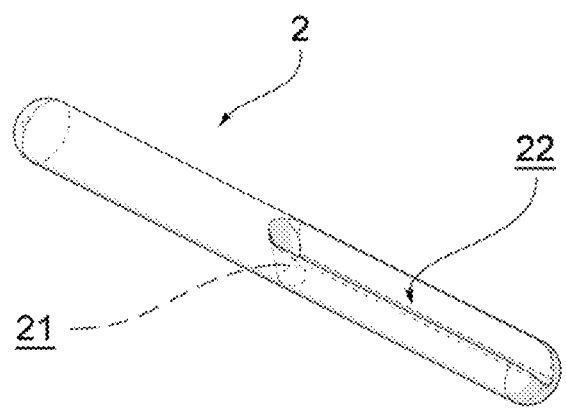
FIG. 4 is an axonometric view of the distal clip in a further embodiment comprising a slot which is adapted to receive the tie rod element and has a V-shaped cross section.
Figure 5:
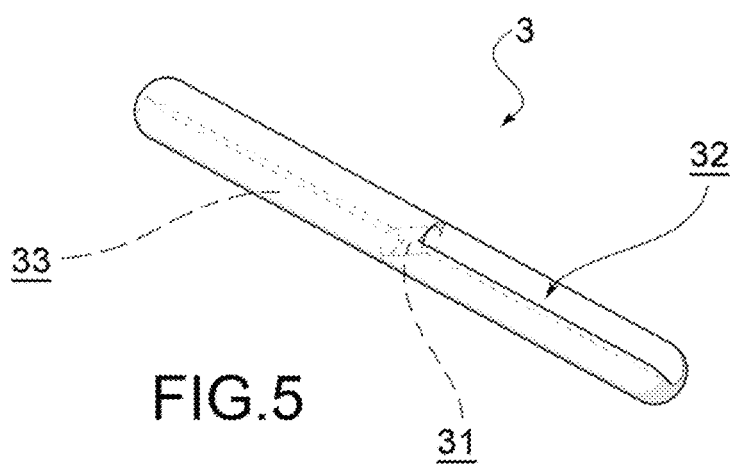
FIG. 5 is an axonometric view of the proximal clip in a further embodiment.
Figure 5A:
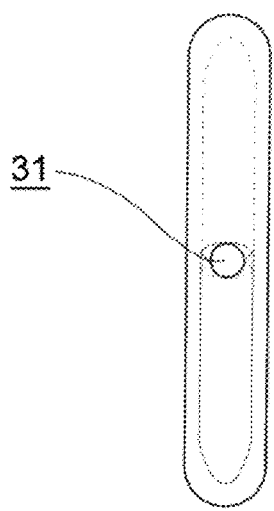
FIGS. 5A and 5B show two embodiments of the hole in the proximal clip.
Figure 5B:
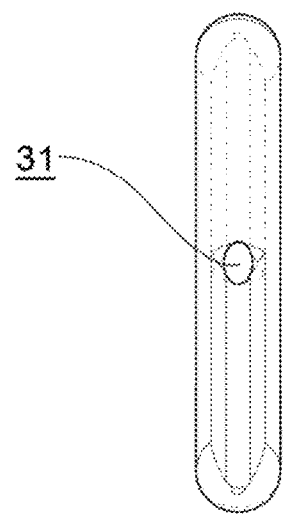

In one embodiment, shown in FIGS. 4 and 5, the housing 22, 32, 33 has a triangular or V-shaped cross section.

Figure 9B:
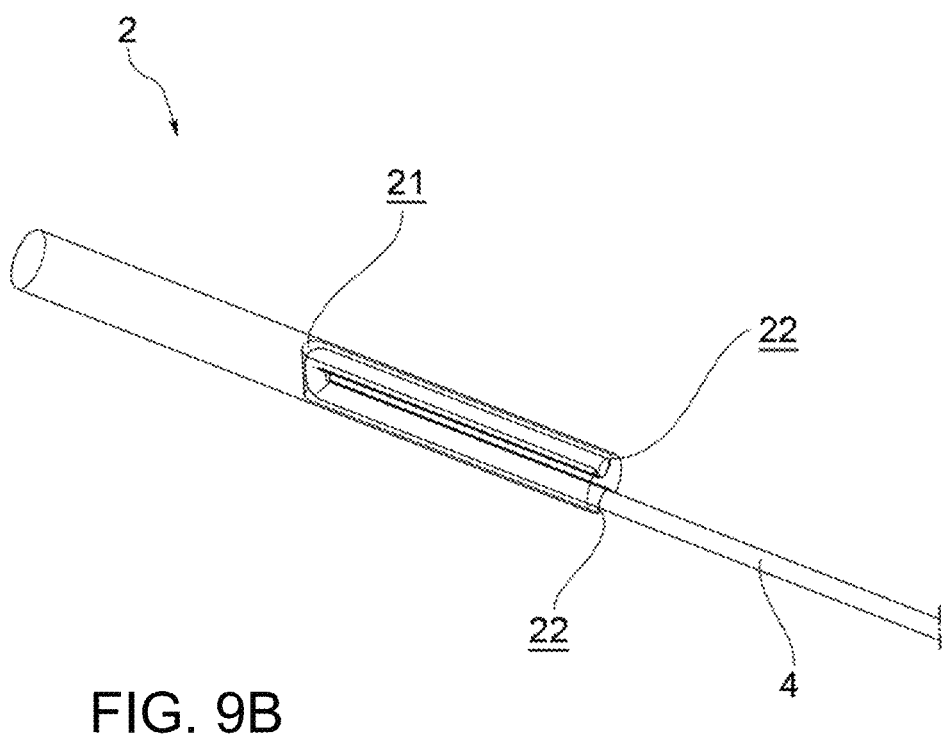

In one embodiment, shown in FIG. 9A, the distal clip 2 is provided with a couple of proximal housings 22, positioned parallel one to each other on both sides of the distal clip. In this configuration, as shown in FIG. 9B, the tie rod 4 runs into a first to proximal housing 22, crosses through the seat 21, and is fixed into the second proximal housing 22. In a farther example, the distal clip 2 is provided with a proximal housing 22 and a distal housing. In this configuration, the tie rod 4 runs into the proximal housing 22, crosses through the seat 21, and is fixed into the distal housing. The solution of fixing the tie rod 4 into a housing allows a secure and reliable fixing, and improves control of the direction of the distal clip 2 in the releasing phase (FIG. 1B).

Figure 7:
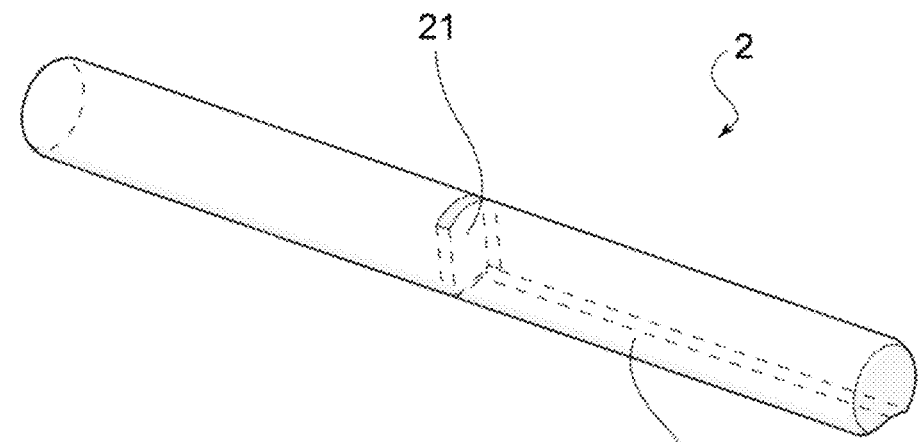
FIG. 7 is an axonometric view of the distal clip in a further embodiment.
Figure 8A:
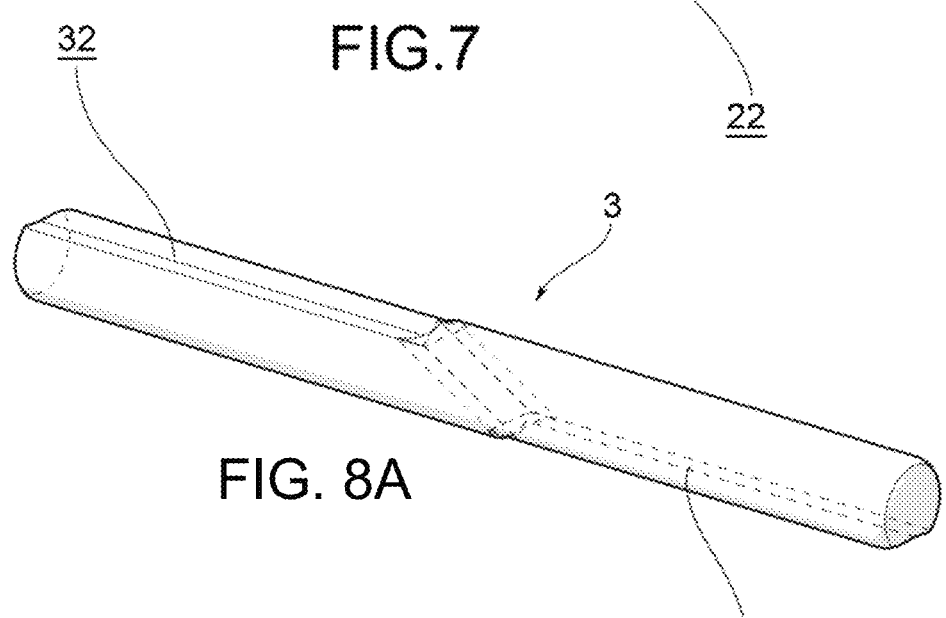
FIGS. 8A and 8B are an axonometric view and a cross-sectional view, respectively, of the proximal clip in a further embodiment.
Figure 8B:
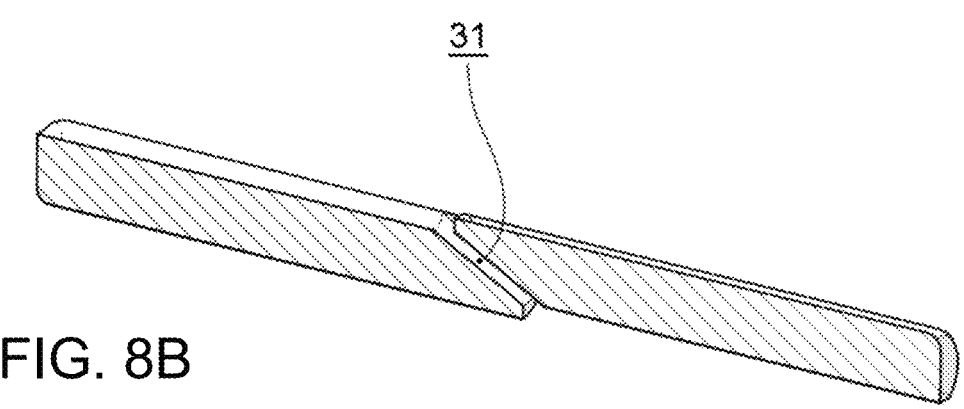

In one embodiment, shown in FIGS. 7 and 8A, the housing 22, 32, 33 is a longitudinal flattened portion or a C-shaped or crescent-shaped recess.

The housing 22, 32, 33 comprises an inlet end to the clip 2, 3 and an end that traverses the clip 2, 3 and flows into the seat 21, 31.

The distal clip 2 therefore comprises a path for the tie rod 4 that starts from the seat 21 and continues along the housing 22. The path for the tie rod 4 occupies approximately half of the length of the distal clip 2.

In one embodiment, the distal clip 2 also comprises a distal housing used as a further compartment (in addition to the seat 21) for fastening the tie rod 4. In this example, therefore, the distal clip 2 comprises a path for the tie rod 4 that starts from the distal housing and continues into the seat 21 through the clip in order to exit from the opposite side and continue along the housing 22. In this case, the path for the tie rod 4 therefore occupies more than half of the length of the distal clip 2.

The proximal clip 3 comprises a path for the tie rod 4 that starts from the housing 32 and continues into the seat 31 through the clip in order to exit from the opposite side and continue along the housing 33. The path for the tie rod 4 occupies the entire length of the proximal clip 3.

Figure 6B:
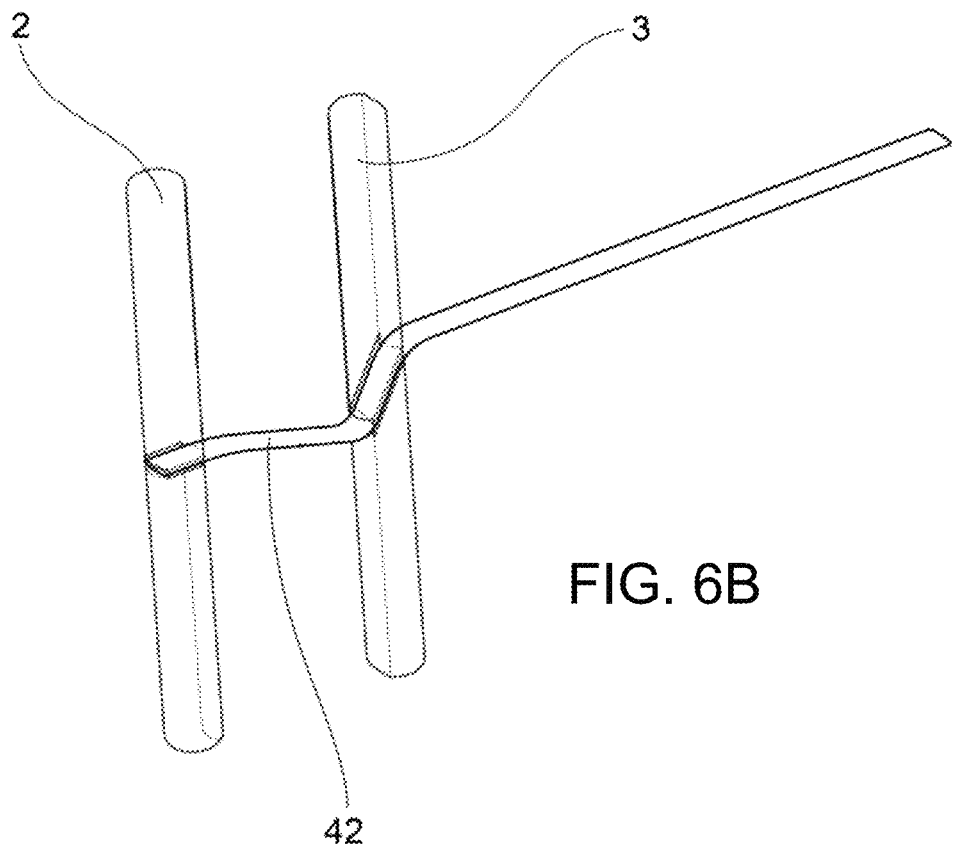

In the embodiment shown in FIGS. 6A and 6B in which the tie rod 4 has a flattened cross section, the seat 21, 31 into which the tie rod 4 is inserted is rectangular and may be arranged longitudinally or transversely with respect to the clip 2, 3. Moreover, in this embodiment, the housing 22, 32, 33 in which the tie rod 4 is positioned when the clips 2, 3 are inside the main body 1 may be C-shaped or crescent-shaped.

The percutaneous device 100 comprises a handle 7 which extends predominantly longitudinally, is formed by two half-shells mechanically connected together, and is connected to the proximal portion of the main body 1.

The handle 7 comprises a handle body 71 provided with a track 73 in which an operating lever 72 for operating the clips 2, 3 and the tie rod 4 is slidably accommodated.

Figure 16A:
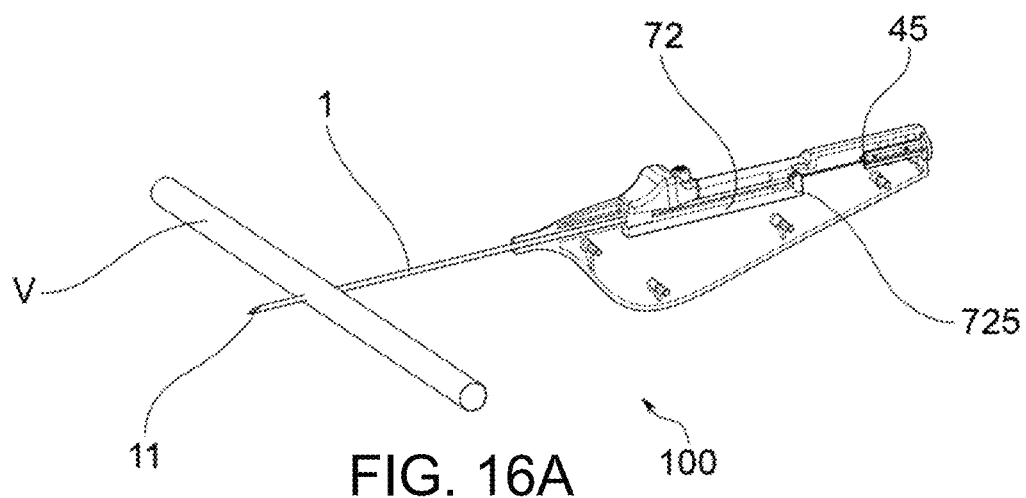
FIGS. 16A to 16F show the steps of the process for closing a venous vessel by means of the device in FIG. 14, and in particular.
Figure 18A:
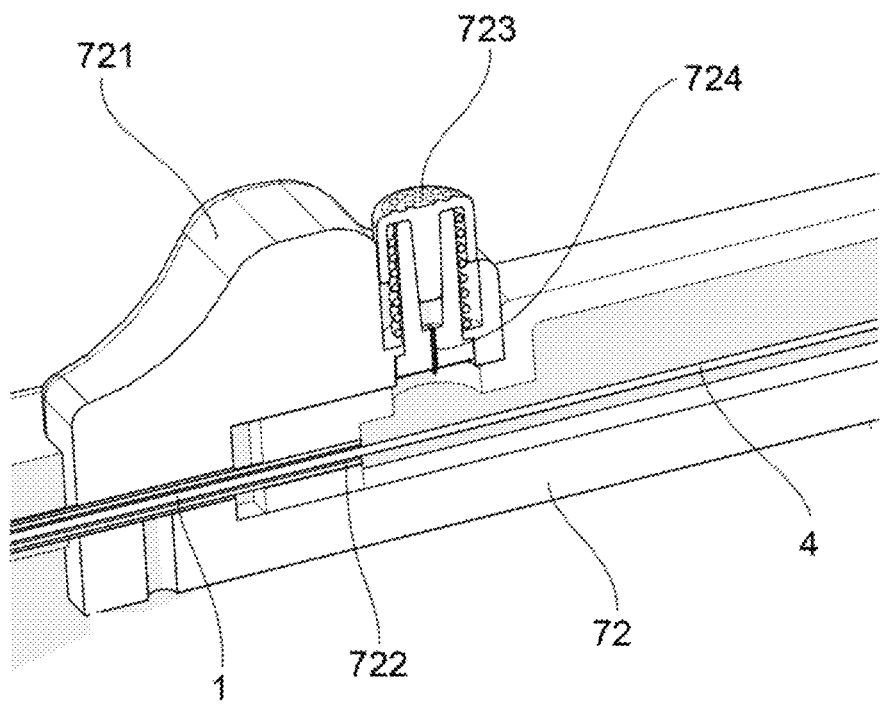
FIGS. 18A and 18B are detailed views of the proximal cutting system for cutting the tie rod of the clips: deactivated cutting system (FIG. 18A) and activated cutting system (FIG. 21 18B).

The operating lever 72, which may be seen in detail in FIG. 18A, extends predominantly longitudinally and preferably comprises a slider 721 shaped so as to facilitate gripping and sliding of the slider inside the track 73. In the embodiment of FIG. 16a the handle 7 comprises a slider 721 on an upper side. In a further embodiment the handle 7 comprises a slider 721 on an upper side and an opposed slider on a lower side; in said example both the sliders are connected to the lever 72.

Figure 16B:
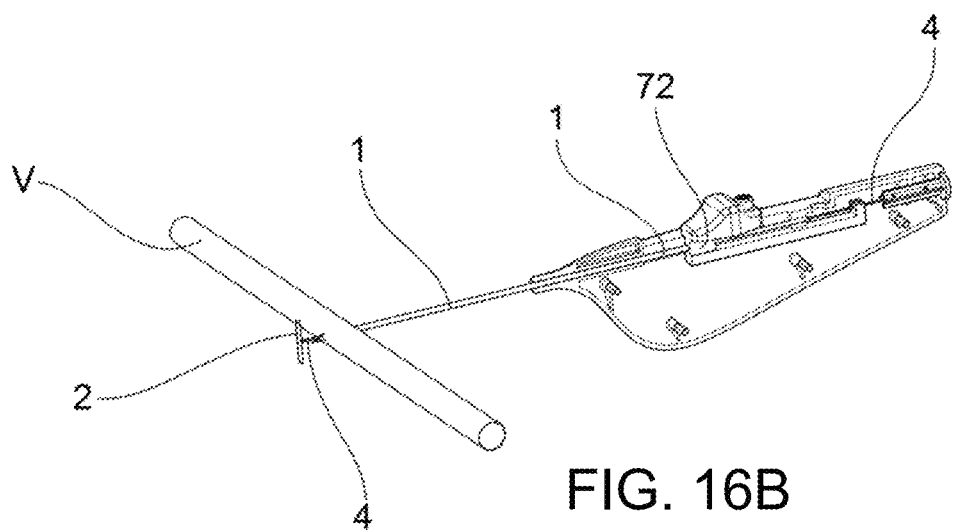

The main body 1 is integral with the operating lever 72, which means that retracting the operating lever 72 also retracts the main body 1, as shown in FIG. 16B.

The operating lever 72 comprises at least one seat 722 for the passageway of the tie rod 4, such that the lever may slide on the tie rod 4.

Figure 16C:
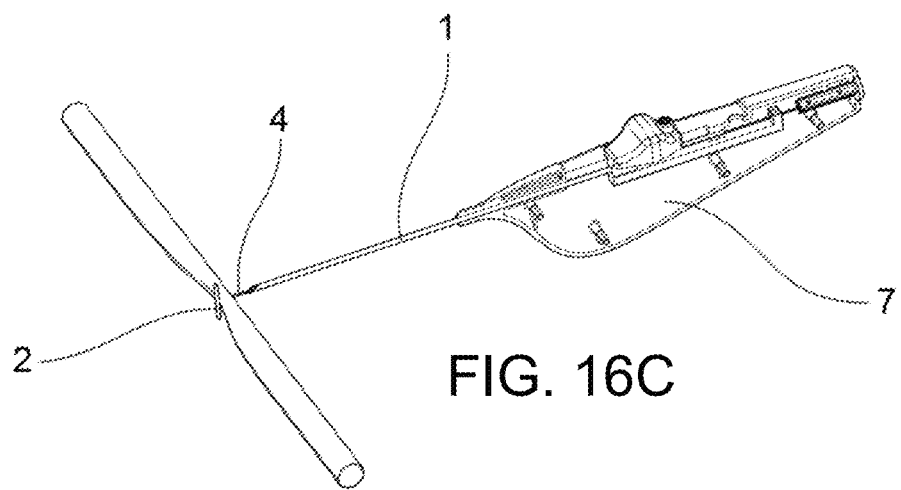
Figure 16D:
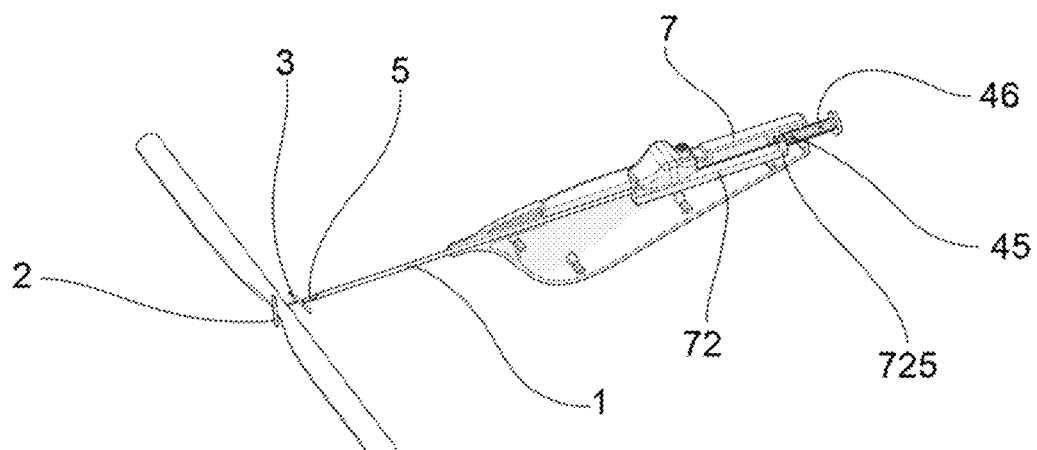

The operating lever 72 comprises, at the rear, a lever stop 725 adapted to abut against a relevant tie rod stop 46 such that the operating lever 72 becomes integral with the tie rod 4 and retracting the operating lever 72 also retracts the tie rod 4, as may be seen in FIG. 16D.

Figure 16E:
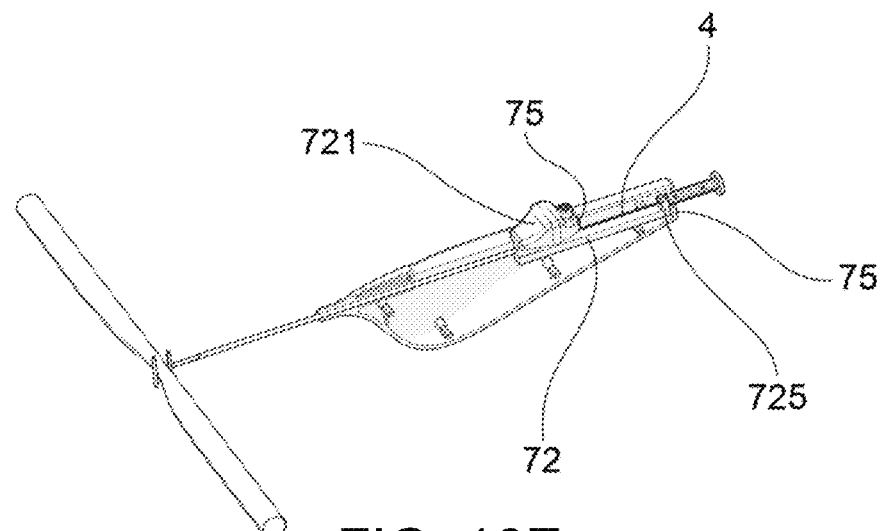

The handle 7 comprises a handle stop 75 configured to abut against the lever stop 725 or against the slider 721 such that the operating lever 72 may not be retracted any further, as may be seen in FIG. 16E.

The tie rod 4 is also provided with a traction element configured to pull the tie rod 4 with respect to the handle 7.

Figure 14:
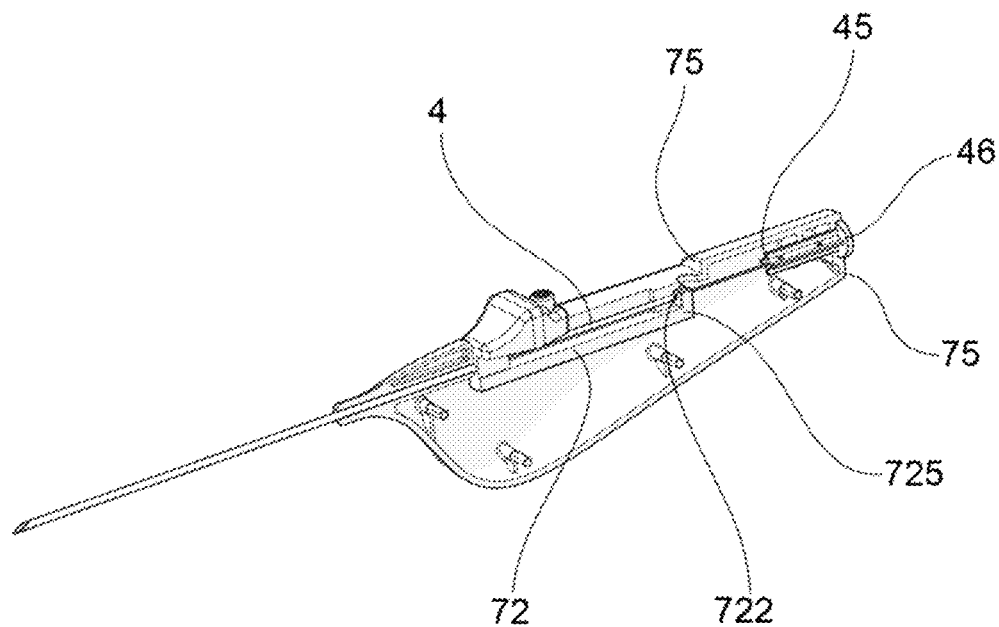
FIG. 14 is a cross-sectional view of a device according to the present invention that is provided with a handle in one embodiment.

In the variant in FIG. 14, the traction element 45 is connected to the proximal end 43 of the tie rod 4. The traction element 45 at least partially exits the handle 7 in order to be gripped and optionally pulled by the medical professional, as in FIG. 16F.

Figure 15:
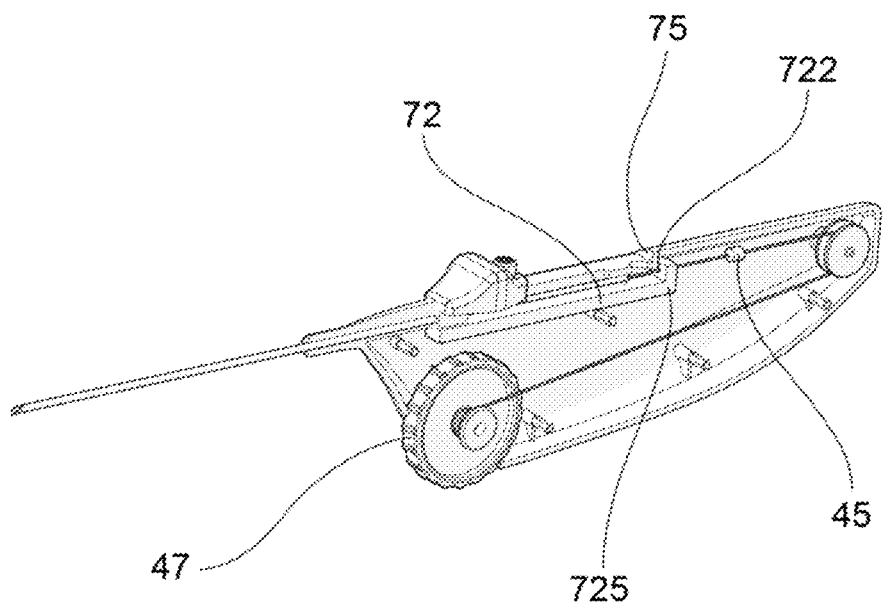
FIG. 15 is a cross-sectional view of a device according to the present invention provided with a handle in a further embodiment.

In the variant in FIG. 15, the traction element is a wheel 47 connected to the proximal end 43 of the tie rod 4. The wheel 47 at least partially exits from the handle 7 in order to be optionally rotated by the medical professional.

Figure 18B:
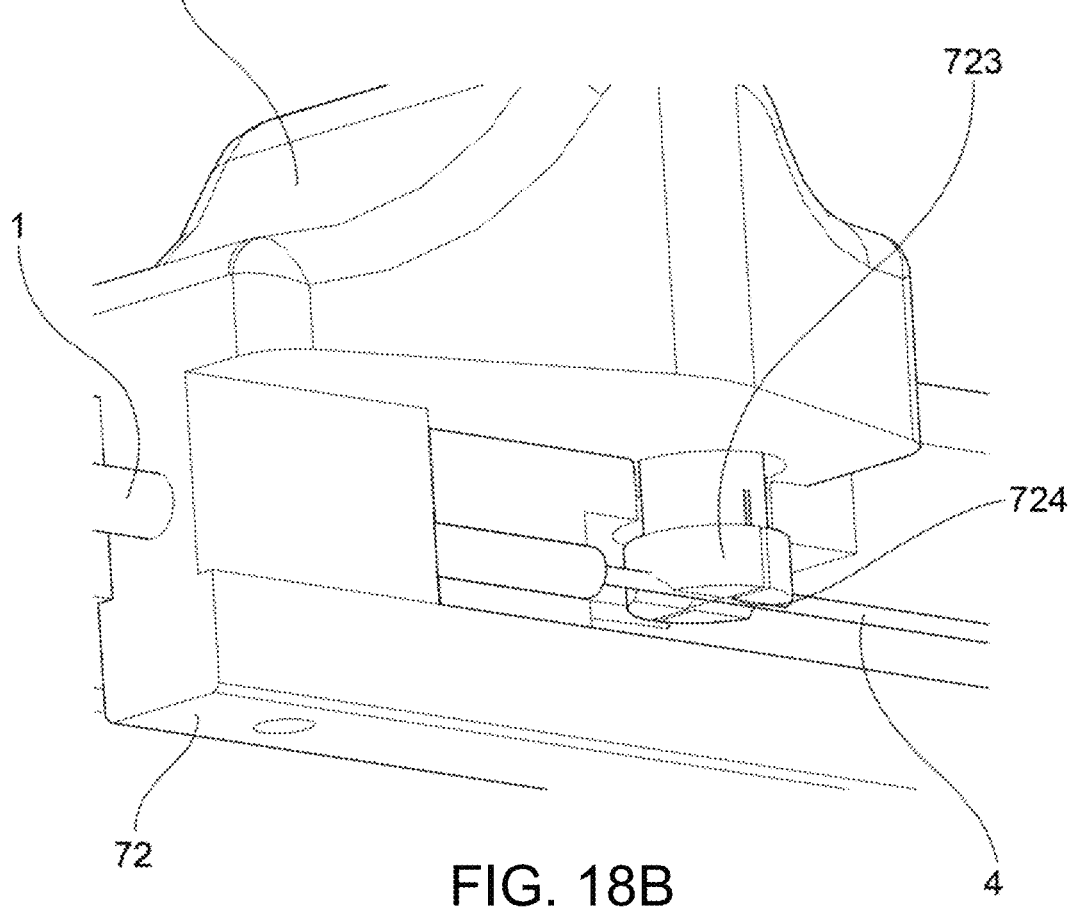

The operating lever 72 comprises, in proximity to the slider 721, a cutting button 723 provided with a blade 724 adapted to sever the tie rod 4. The cutting button 723 is vertically slidable between a rest position (FIG. 18A) in which the blade 724 is spaced apart from the tie rod 4 and a cutting position (FIG. 18B) in which the blade 724 is pushed against the tie rod 4 in order to sever it.

Figure 17A:
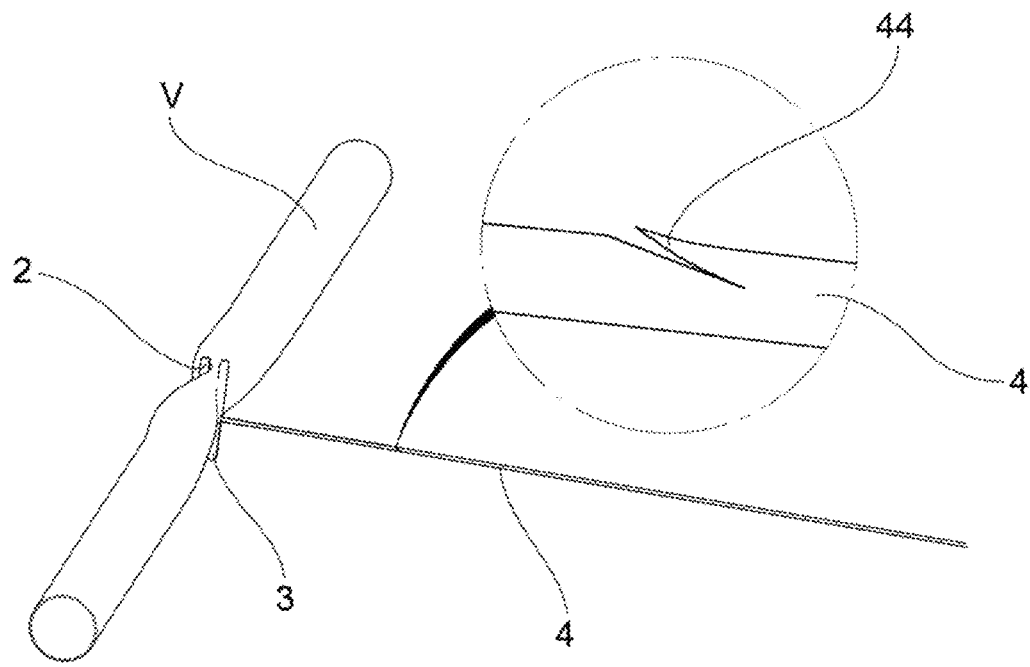
FIGS. 17A and 17B show the final steps of the process for closing a venous vessel, in particular weakening the tie rod of the clips and breaking the tie rod in order to completely release the clips.
Figure 17B:
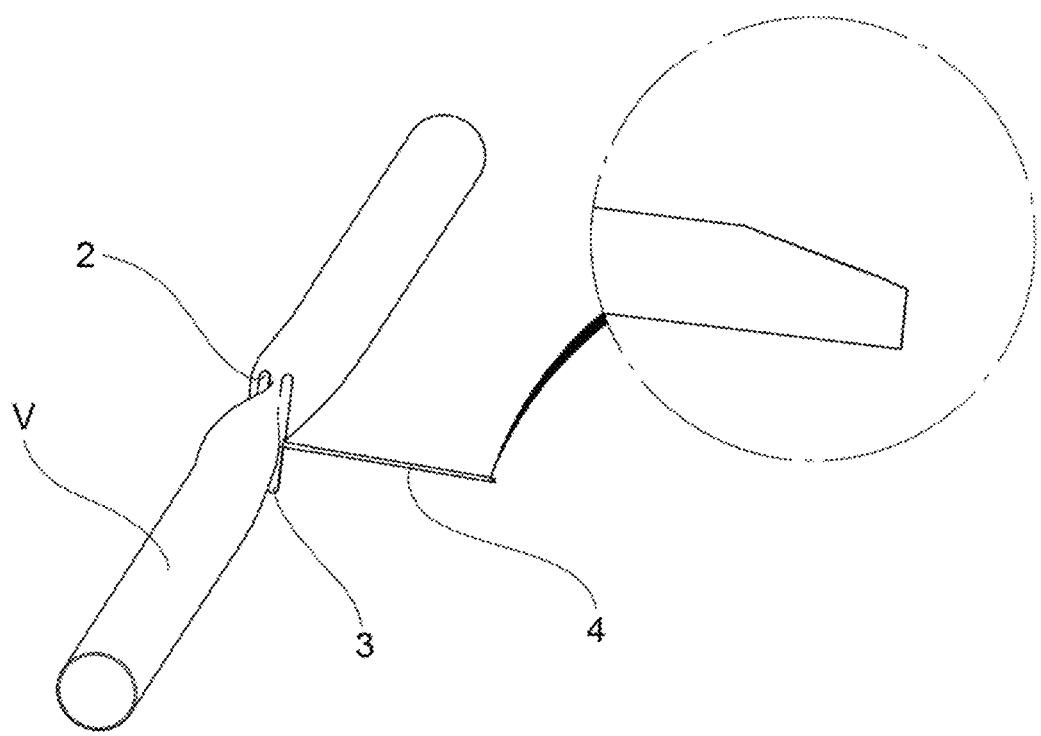

In one embodiment shown in FIG. 17A, the tie rod 4 is provided, proximally with respect to the proximal clip 3, with a predetermined breaking point 44, for example a pre-incision or a weakened portion, that is adapted to yield in response to a certain traction force exerted on the tie rod 4. Said predetermined breaking point 44 is a calibrated point of weakness that makes it possible to only release the pair of clips after an optimal traction force has been exerted, in order to clamp and therefore occlude the vessel. This solution allows as little of the tie rod 4 as possible to be left inside the body of the patient after the vessel has been closed, as shown in FIG. 17B.

The sequence of figures from 16A to 16F shows the use of the device 100 in order to close a blood vessel.

As shown in FIG. 16A, firstly the main body 1 is introduced percutaneously by means of the needle tip 11. The tip 11 then punctures the wall of the blood vessel V and passes through said vessel from one side to the other. During insertion of the device 100, the longitudinal axis of the clips 2, 3 is in line with the longitudinal axis of the main body 1.

At this point, as shown in FIG. 16B, the distal clip 2, and with it also part of the tie rod 4, is made to exit from the distal opening 12 in the main body 1. The distal clip 2 is made to exit by retracting the operating lever 72 and the main body 1 therewith, while keeping the proximal clip 3 and the abutment element 5 in position.

The tie rod 4 is then pulled, as may be seen in FIG. 16C, by pulling the handle 7, in order to correctly position the distal clip 2 against the outer wall of the vessel V. At this point, the distal clip 2 is arranged externally and substantially transversely with respect to the main body 1. Ultrasonic checks are used to verify that the distal clip 2 is abutting transversely against the distal wall of the blood vessel V.

At this point, as shown in FIG. 16D, the proximal clip 3, and with it also part of the tie rod 4, is also made to exit the distal opening 12 in the main body 1 in the same manner as the distal clip 2. The proximal clip 3 is made to exit by retracting the operating lever 72 and the main body 1 therewith, while keeping the abutment element 5 in position.

The tie rod 4 is then pulled, as may be seen in FIG. 16E, by pulling the handle 7, in order to correctly position the proximal clip 3 against the outer wall of the vessel V. At this point, the proximal clip 3 is also arranged externally and substantially transversely with respect to the main body 1.

Figure 16F:
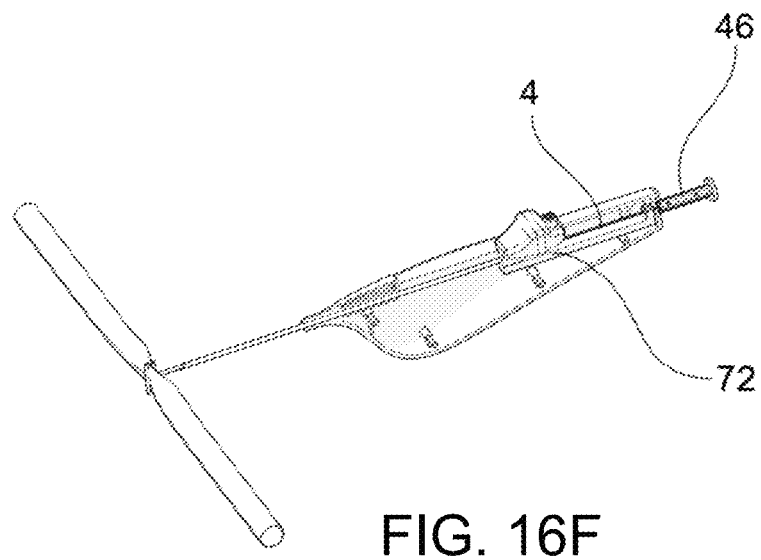

At this point, the tie rod 4 is also pulled, as may be seen in FIG. 16F, in order to correctly clamp the vessel between the distal clip 2 and the proximal clip 3. The tie rod 4 is optionally pulled by means of the traction element 45 or by rotating the wheel 47.

It should be noted that the tie rod slides into the seat 21 of the proximal clip 3 with a calibrated friction that allows the clips 2, 3 to clamp.

Figure 13A:
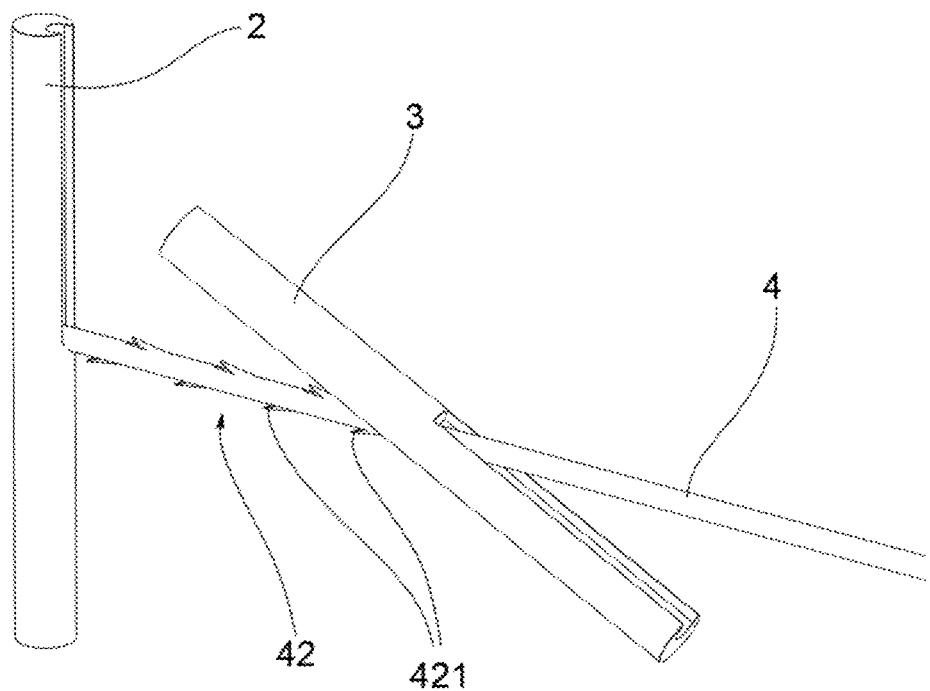
FIGS. 13A and 13B show the device according to the present invention having a further configuration of the portion of the tie rod arranged between the clips.
Figure 13B:
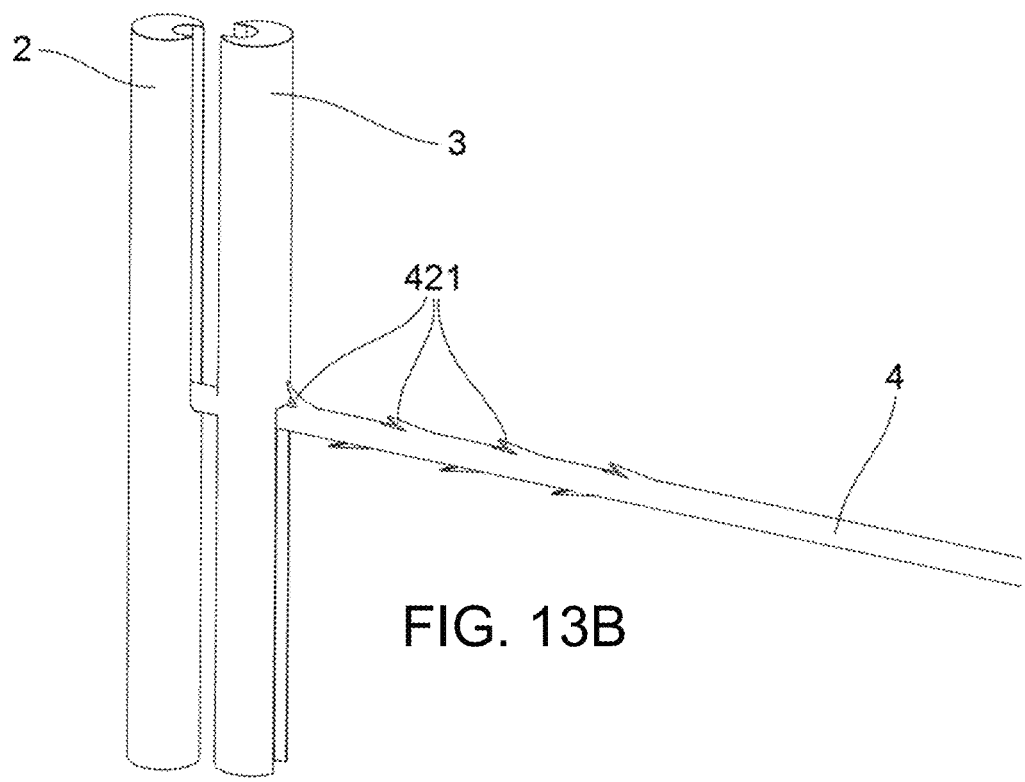

The tie rod 4 is preferably provided with a radial dimension, for example a flattened portion or a thickened portion in a proximal position, so as to prevent the tie rod from being able to reenter the seat 31 of the proximal clip 3 once this radial dimension has exited therefrom. This solution makes it possible to maintain the correct clamping of the vessel between the distal clip 2 and the proximal clip 3, thus avoiding the need to produce a node on the tie rod that has to be pushed into position. FIGS. 13A and 13B show the tie rod 4, and in particular at least the intermediate portion 42 arranged between the clips, having securing fins 421 suitable for preventing the moving back of the proximal clip 3 during the clamping phase of the vessel (FIG. 16F).

At this point, it is possible to sever the tie rod 4 by means of actuating the cutting button 723 present on the handle or by means of pulling further if a predetermined breaking point 44 on the tie rod 4 is used.

The percutaneous device according to the present invention innovatively makes it possible to carry out operations to intercept and/or close a blood vessel percutaneously in a simplified manner, which requires reduced manual ability which is not necessarily surgical.

In the percutaneous device according to this invention, as a result of the housings 22, 32, 33 and the respective paths provided on the clips 2, 3, the tie rod 4 advantageously does not interfere with the correct sliding of the clips 2, 3 inside the main body 1.

The percutaneous device according to the present invention advantageously makes it possible to implement a mechanical method for closing a vein, or in general a blood vessel, even a large-caliber vessel, by means of closing or "clamping" on the outer wall of the blood vessel, which method is carried out percutaneously. It is therefore possible to perform ultrasound-guided obstruction of a vein by means of percutaneous clamping.

Advantageously, as a result of using a percutaneous device according to the present invention, the operating times and the impact on patient acceptance (or compliance) are drastically reduced by comparison with "open" surgery techniques.

The clips 2, 3 may advantageously be made of resorbable material, and may remain in position in order to guarantee the interruption of the venous blood flow while not interrupting the anatomical continuity of the vascular structure.

The device according to the present invention advantageously has various fields of application such as: superficial venous insufficiency; any case in which it is necessary to "ligate" or interrupt a venous tract; sapheno-femoral crossectomy; sapheno-popliteal crossectomy; interruption of varicose collaterals; interruption of incontinent perforating veins; segmentation of the saphenous reflux.

The process may be intended as a simple isolated surgical procedure carried out on one or more sites, or may be a process carried out in association with other operations. An example of this is the interruption of the sapheno-femoral junction carried out in association with a procedure to ablate the great saphenous vein that is carried out using physical or chemical techniques.

It is to be understood that a person skilled in the art may make modifications to the product described above, all of which are contained within the scope of protection as described and claimed herein.

What is claimed is:

1. A percutaneous device for closing blood vessels, comprising:
   an internally hollow main body comprising a distal tip having a distal opening;
   a distal clip and a proximal clip slidably accommodated inside the internally hollow main body, said distal clip and proximal clip being connected to each other by a tie rod, wherein the distal clip is fastened to the tie rod and the proximal clip slides with respect to the tie rod;
   an abutment element for the distal clip and proximal clip, slidably accommodated inside the internally hollow main body, said abutment element comprising a longitudinal passageway for the tie rod;
   a handle, connected to the internally hollow main body, to maneuver said distal clip, proximal clip, abutment element, and tie rod, wherein the distal clip comprises a needle-shaped distal perforation end that protrudes from the distal opening of the main body;

wherein the distal clip comprises at least one proximal longitudinal groove formed on an outer surface of the distal clip, and the proximal clip comprises a distal longitudinal groove formed on an outer surface of the proximal clip and a proximal longitudinal groove formed on an outer surface of the proximal clip, and wherein the tie rod is positioned inside said longitudinal grooves when the distal clip and the proximal clip are inserted into the internally hollow main body, and wherein the at least one proximal longitudinal groove of the distal clip occupies at least a proximal portion of said distal clip, the distal longitudinal groove of the proximal clip occupies at least a distal portion of said proximal clip and the proximal longitudinal groove of the proximal clip occupies at least a proximal portion of said proximal clip.

2. The percutaneous device of claim 1, wherein the distal clip comprises a distal seat, in which the tie rod is fastened, and wherein said distal seat transversally crosses the distal clip, perpendicularly.

3. The percutaneous device of claim 1, wherein the proximal clip comprises a proximal seat in which the tie rod is slidably inserted, and said proximal seat is a through hole which transversely crosses the proximal clip, obliquely.

4. The percutaneous device of claim 1, wherein the distal clip, the proximal clip and the tie rod are made of resorbable material.

5. The percutaneous device of claim 1, wherein the abutment element comprises a distal end sized to be housed in the proximal longitudinal groove of the proximal clip.

6. The percutaneous device of claim 1, wherein the distal clip and the proximal clip comprise faced ends having parallel inclined faces to allow partial overlapping of said distal and proximal clips when inserted into the internally hollow main body.

7. The percutaneous device of claim 1, wherein the tie rod comprises securing fins at least in an intermediate portion arranged between the distal and proximal clips when inserted into the internally hollow main body.

8. The percutaneous device of claim 1, wherein the internally hollow main body comprises a distal perforation tip having a notch extending in proximal direction and sized to at least partially house the distal clip.

\* \* \* \* \*